US007014860B1

(12) United States Patent
Kawata et al.

(10) Patent No.: US 7,014,860 B1
(45) Date of Patent: Mar. 21, 2006

(54) HYALURONIC ACID GEL, PROCESS FOR PRODUCING THE SAME, AND MEDICAL MATERIAL CONTAINING THE SAME

(75) Inventors: Masatoshi Kawata, Tokyo (JP); Akio Okamoto, Tokyo (JP); Yoshiaki Miyata, Tokyo (JP); Kazuhiro Ohshima, Tokyo (JP); Osamu Yamamoto, Tokyo (JP); Teruzou Miyoshi, Tokyo (JP); Kazuhiko Arai, Niigata (JP); Hironoshin Kitagawa, Tokyo (JP); Toshihiko Umeda, Tokyo (JP); Hiroshi Kaneko, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/182,467

(22) PCT Filed: Feb. 3, 2000

(86) PCT No.: PCT/JP00/00582

§ 371 (c)(1),
(2), (4) Date: Jul. 29, 2002

(87) PCT Pub. No.: WO01/57093

PCT Pub. Date: Aug. 9, 2001

(51) Int. Cl.
A61F 13/00 (2006.01)
(52) U.S. Cl. ............... 424/422; 424/423; 424/426; 424/484; 424/485; 424/78.08; 424/78.17

(58) Field of Classification Search ............... 424/422, 424/423, 426, 484, 485, 78.08, 78
See application file for complete search history.

(56) References Cited

U.S. PATENT DOCUMENTS

| 4,795,741 | A | * | 1/1989 | Leshchiner et al. ............ 514/21 |
| 5,166,331 | A | * | 11/1992 | della Valle et al. ......... 536/55.1 |
| 5,409,904 | A | * | 4/1995 | Hecht et al. ................... 514/23 |
| 5,958,443 | A | | 9/1999 | Viegas et al. |
| 6,387,413 | B1 | | 5/2002 | Miyata et al. |
| 6,635,267 | B1 | * | 10/2003 | Miyoshi et al. ............. 424/422 |
| 6,638,538 | B1 | * | 10/2003 | Hashimoto et al. ......... 424/548 |
| 6,790,461 | B1 | * | 9/2004 | Miyata et al. .............. 424/548 |

FOREIGN PATENT DOCUMENTS

| JP | 5-58881 | 3/1993 |
| JP | 9-59303 | 3/1997 |
| WO | WO 99/10385 | 3/1999 |

* cited by examiner

Primary Examiner—Thurman K. Page
Assistant Examiner—Isis Ghali
(74) Attorney, Agent, or Firm—Oblon, Spivak, McClelland, Maier & Neustadt, P.C.

(57) ABSTRACT

Production of a hyaluronic acid gel, which comprises keeping hyaluronic acid in water at a hyaluronic acid concentration of at least 5 wt % in the presence of an acid component in an amount at least equimolar with the carboxyl groups in the hyaluronic acid.

21 Claims, 2 Drawing Sheets

HYALURONIC ACID GEL, PROCESS FOR PRODUCING THE SAME, AND MEDICAL MATERIAL CONTAINING THE SAME

TECHNICAL FIELD

The present invention relates to a novel hyaluronic acid gel with transparency and a method of its production, and further, to a biomedical material with good biocompatibility.

BACKGROUND ART

Hyaluronic acid is a linear macromolecular polysaccharide consisting of alternately bonded β-D-N-acetylglucoamine and β-D-glucuronic acid. Hyaluronic acid is found not only in connective tissues of mammals but also in cockscombs and the capsules of *Streptococci*. Hyaluronic acid is obtainable not only by extraction from cockscombs and umbilical cords, but also as purified products from the culture broth of *streptococci*.

Natural hyaluronic acid is polydisperse in respect of molecular weight and is known to show excellent biocompatibility even when implanted or injected into the body by virtue of the absence of species and organ specificity. However, because of the relatively short in vivo residence time of hyaluronic acid solution in biological application, improvement of the persistency of hyaluronic acid by chemical crosslinking with various chemical modifiers has been attempted to broaden its use for medical materials.

(I) Concerning the joints, synovial fluid supplies nutrition to the articular cartilage and has incomparable functions as a lubricant and a shock absorber. It is clarified that its excellent viscoelastisity heavily owes to one of the main components, hyaluronic acid.

Concentration and molecular weight analyses of hyaluronic acid demonstrated the concentration and molecular weight of hyaluronic acid in the synovial fluid from patients with arthritis such as osteoarthritis and chronic articular rheumatism generally tend to lower than in normal synovial fluid, and the lower concentration and molecular weight of hyaluronic acid are closely associated with development of locomotor dysfunction and pain attributable to the weaker lubricating action and the weaker protecting action on the surface of the articular cartilage of synovial fluid.

Injection of high molecular weight hyaluronic acid solution (Artz: from Seikagaku Corporation, average molecular weight 900000; Hyalgan: from Fidia, average molecular weight<500000) into diseased joints has been widely adopted as an effective measure for osteoarthritis among those articular diseases, and the source of high purity hyaluronic acid preparations for this purpose is cockscombs.

Such hyaluronic acid preparations from cockscombs are biologically inherent and quite safe but usually have to be administered as frequently as several to 10 times to show significant therapeutic effect.

Persistency tests on rabbits revealed that hyaluronic acid with a molecular weight of less than 1000000 administered into the knee joint cavities disappears from the knee joint cavities in 1 to 3 days and suggest the need of frequent administrations (Blood Coagulation and Fibrinolysis, vol 12, 173, 1992).

On the other hand, the molecular weight of hyaluronic acid found in the living body is reported to be as high as millions to 10000000, and a crosslinked hyaluronic acid derivative [Hylan: from Biomatrix] obtained by treatment with a chemical crosslinker has been developed as a therapeutic agent for knee joints with the idea that high molecular weight hyaluronic acid closer to the biologically intact one is likely to have higher effect.

Reportedly, the crosslinked hyaluronic acid persisted for a period as long as 20 to 30 days after administration into rabbit knee joint cavities in the above-mentioned persistency tests and produced sufficient effect when administered three times in clinical tests, and is practically used as a therapeutic agent for arthritis (Journal of Rheumatology vol. 20, 16, 1993).

(II) Next, concerning emboli, treatments through embolization are known to effective for various diseases such as angiopathy, paraplastic aneurysm and varix. Obstruction of arteries as the nourishing channels for tumours is also effective in tumour treatment.

Some proposals have been made for embolization. For example, a balloon embolization method using a balloon-tip catheter has been developed (W. Taki et al., Surg. Neurol, Vol. 12, 363, 1979). In addition, a method in which 2-hydroxyethyl methacrylate (HEMA) is introduced into a balloon together with a polymerization catalyst through a catheter is also known (W. Taki et al., Surg. Neurol, Vol. 13, 140, 1980).

For cancer treatment through embolization, use of cisplatin-containing chitin (Tahara et al., Cancer and Chemotherapy, vol. 21(13), 2225, 1994), use of poly(benzyl 1-glutamate) microspheres carrying cisplatin (Li C et al., Parm, Res., Vol. 11(12), 1792, 1994) and use of SMANCS and Lipiodol suspension together with gelatin sponge as a embolizing material (Nakamura et al., Cancer and Chemotherapy, vol. 22(11), 1390, 1996) have been reported. In addition, poly(DL-lactate) microspheres are reported as a suitable material for use in embolismic chemotherapy in combination with continuous injection of a chemotherapeutic agent (Flandroy P et al., J Control Release, Vol. 44(2/3), 153, 1997) while it is mentioned that they have to biodegrade in a couple of days so that when this therapy is practiced repeatedly.

There are a lot of problems such as the short time obstruction in the balloon embolization due to shriveling of the balloon as a bar to production of satisfactory effect and the possibility of polymerization of monomers such as HEMA inside the catheter. Most embolizing materials used in embolismic chemotherapy are synthetically available and hardly biodegradable and doubtful in respect of biocompatibility. Poly(DL-lactate) microspheres, though biodegradable, do not guarantee complete safety when repeatedly administered.

Though highly biocompatible hyaluronic acid has no problem with safety, hyaluronic acid does not embolize when merely administered in the form of solution, and is required to have improved local persistency.

(III) Concerning soft tissues, the idea of injecting various materials to repair or swell soft tissues has rapidly developed since the invention of the subcutaneous injection needle, and a number of materials have been injected into human bodies to remedy soft tissues and skins. Among them, liquid silicone has been used widely for injection but is not used as much recently as it used to be due to its side effects such as skin ulceration attributable to its long retention time. Collagen has also been injected so far in various forms such as chemically crosslinked forms and fibrous forms. Crosslinked solid collagen requires incision to be injected and has problems in plasticity and flexibility. There is a disclosure about fibrous collagen in U.S. Pat. No. 3,949,073.

However, it shrinks in volume as its liquid components are absorbed and has to be supplemented. Injectable types of collagen like this can hardly be freed of contaminants such as immunity substances, are costly and do not necessarily have appropriate physical properties.

Hyaluronic acid has also been attempted as an injection for soft tissues (Ann. Plast. Surg., Vol. 38, 308, 1997). Because hyaluronic acid in solution is rapidly absorbed in vivo, various methods for chemical crosslinking of hyaluronic acid have been attempted to improve persistency and retention in soft tissues (U.S. Pat. No. 4,582,865, JP-B-6-37575, JP-A-7-97401, JP-A-60-130601).

And hylan B gel is commercially available as Hylaform in Europe (The Chemistry Biology and Medical Application of Hyaluronan and its Derivatives Vol. 72, p 278, PORTLAND PRESS).

(IV) Next, reference will be made to the posterior part of the eyeball, especially the retina bordered on the vitreous body. The retina marks the posterior boundary of the intraocular space, while the lens and the ciliary body mark the anterior boundary. The retina consists of two layers, the receptor layer of photosensitive cells in contact with the vitreous humor and the layer of pigment epithelial cells adjacent to the choroid. Liquid infusion into the receptor layer causes retinal detachment, separating the two layers of the retina.

For treatment of retinal detachment, the peeled retina is brought into contact with the pigmented epithelial layer and fastened by photocoagulation or cryocoagulation. The contact is achieved by pressing an inward buckle against the sclera and the choroids from outside or by generating pressure from vitreous humor onto the retina through volume expansion of vitreous humor by injection.

In the latter case, when vitreous humor has to be removed partly or completely due to too much spilt blood for reabsorption or inward growth of the retina accompanying retinal detachment, various materials have been attempted as artificial vitreous bodies.

These artificial vitreous bodies are intended to maintain the shape of the eyeball and bring back the retina in position by pressing the retina against the pigmented epithelium in the vitreous chamber for a while.

As artificial vitreous bodies, physiological saline, glycerin, animal vitreous bodies, air, various gases, polyvinyl alcohol, collagen gel, silicone oil, hyaluronic acid and perfluorocarbons may be mentioned, and air, gases such as sulfur hexafluoride, silicone oil, liquid perfluorocarbons such as perfluorooctane and perfluorodecalin are generally used now.

Various expansive gases are used as artificial vitreous bodies by themselves or in mixtures with air, and have proven to be useful (American Journal of Opht hyaluronic acid lmology, Vol. 98, 180, 1984).

However, they sometimes cause complications such as increase of intraocular pressure and coreclisis attributable to gas expansion or keratoleukoma attributable to their contact with the corneal endothelium and impose on patients a heavy burden of keeping their faces down for a long time.

Silicone oil maintains the intraocular space for a longer time than gases by virtue of its little absorbability and accelerates adhesion of the retina effectively (Retina, Vol. 7, 180, 1987), but is used with the proviso that it is drawn out after exertion of the pressing effect on the retina. Further, it is said to have serious problems of cataract, glaucoma and toxic effects on the ocular tissue (Ophthalmology, Vol. 27, 1081, 1985).

Liquid perfluorocarbons as artificial vitreous bodies are proved to cause complications such as proliferative vitreoretinopathy, cataract and intraocular hypotension and are reported to be more questionable than silicone oil and gases in respect of safety and effectiveness (New Ophthalmology, Vol. 12, 1053, 1995).

Hyaluronic acid has been investigated a lot since Balazs reported its application in the field of ophthalmology (Mod. Probl. Opht hyaluronic acid lmol., Vol. 10, 3 1972) and is widely used in ophthalmic surgery, especially intraocular implantation.

Hyaluronic acid is inherently biogenic and never induces toxic or immunological reactions. However, hyaluronic acid can not exert the effect of maintaining the intraocular space for a long time sufficient for treatment of serious retinal detachment because hyaluronic acid injected into the vitreous chamber dissolves in aqueous humor and is discharged from the eye through the anterior chamber and the fibrous trabecular goniomeshwork without being decomposed.

Though as vitreous injections containing hyaluronic acid, for example, those containing at least 1.5 wt %, preferably from 2 to 2.5 wt % of hyaluronic acid with a molecular weight of at least 900000, preferably 1600000 to 2000000 are disclosed in JP-A-5-184663, they are not retained in the intraocular space [Nippon Ganka Kiyou, vol. 38, 927, 1987], and over 1.5 wt % solution of hyaluronic acid with such a molecular weight strains a syringe when ejected from the syringe into the vitreous body and is not practical.

As mentioned above, improvement of the in vivo retention of hyaluronic acid is essential for its applications, and various chemical crosslinkers have been used to crosslink hyaluronic acid (U.S. Pat. No. 4,582,865, JP-A-60-130601, JP-A-63-281660, JP-B-6-37575, JP-B-6-69481, JP-A-7-97401, JP-A-7-59303). Further, production of a photocrosslinked hyaluronic acid gel by irradiation of a photocrosslinkable hyaluronic acid derivative with ultraviolet light is also known (JP-A-143604).

However, these cross-linked products of hyaluronic acid are not what is called hyaluronic acid any longer, and among the desired properties for materials used in vivo, non-toxicity and non-immunogenicity can not absolutely be secured for them considering procedures for removal of crosslinkers and the difficulty of complete denial of the presence of residual crosslinkers.

The present inventors have found out a simple method of producing a hardly water soluble hyaluronic acid gel made of hyaluronic acid alone for the first time (PCT/JP98/03536). However, the gel is sheet-like, filmy, flaky, spongy or massive and lacks transparency.

Therefore, the present inventors conducted extensive research with an idea that a hardly water soluble transparent material containing hyaluronic acid would be useful and find various medical applications.

To take the advantages of the excellent biocompatibility hyaluronic acid inherently has by itself to the maximum, hardly water soluble hyaluronic acid gels with transparency obtainable without using any chemical crosslinker or modifier are favorable. But such gels had not been developed yet.

On the other hand, for use of hyaluronic acid gels in the field of ophthalmology, especially as artificial vitreous bodies, transparency is required in view of effectiveness. Further, gels with refractive indices closer to that of the vitreous body are preferable (1.3345–1.3348; (Ganka Shinryo Practice, Vol. 22, pp 234, 1996, Bunkodo, Tokyo). However, no gels have been developed yet that have these properties.

The present inventors thought that impartment of transparency to a hardly water soluble hyaluronic acid gel made of hyaluronic acid alone obtained without using any crosslinker or the like would broaden the applications of hyaluronic acid gels and as a result of extensive research for such a gel, have found that hyaluronic acid forms a hyaluronic acid gel when kept in water at a hyaluronic acid concentration of at least 5 wt % in the presence of an acid component in an amount at least equimolar with the carboxylic groups in the hyaluronic acid and that the hyaluronic acid gel obtained in accordance with the present invention is characterized by transparency.

DISCLOSURE OF THE INVENTION

Namely, the present invention provides (1) a method of producing a hyaluronic acid gel, which comprises keeping hyaluronic acid in water at a hyaluronic acid concentration of at least 5 wt % in the presence of an acid component in an amount at least equimolar with the carboxylic groups in the hyaluronic acid, (2) the method of producing a hyaluronic acid gel according to (1), which comprises keeping hyaluronic acid in water at a hyaluronic acid concentration of at least 5 wt % in the presence of an acid component in an amount at least equimolar with the carboxyl groups in the hyaluronic acid at from −10° C. to 30° C., (3) a method of producing a hyaluronic acid gel, which comprises keeping hyaluronic acid in water at a hyaluronic acid concentration of at least 5 wt % in the presence of an acid component in an amount at least equimolar with the carboxyl groups in the hyaluronic acid at from −10° C. to 30° C. to form a hyaluronic acid gel and treating the gel with a neutralizing liquid, (4) a method of producing a hyaluronic acid gel, which comprises keeping an acidic hyaluronic acid aqueous solution containing hyaluronic acid at a concentration of at least 5 wt % and an acid component in an amount at least equimolar with the carboxyl groups in the hyaluronic acid at from −10° C. to 30° C. to form a hyaluronic acid gel and treating the gel with a neutralizing liquid, (5) a method of producing a hyaluronic acid gel, which comprises keeping an acidic hyaluronic acid mixture obtained by mixing hyaluronic acid and an acidic aqueous solution containing an acid component in an amount at least equimolar with the carboxyl groups in the hyaluronic acid to a hyaluronic acid concentration of at least 5 wt % based on the acidic aqueous solution at from −10° C. to 30° C. to form a hyaluronic acid gel and treating the gel with a neutralizing liquid, (6) a method of producing a hyaluronic acid gel, which comprises keeping hyaluronic acid impregnated with an acidic aqueous solution containing an acid component in an amount at least equimolar with the carboxyl groups in the hyaluronic acid to a hyaluronic acid concentration of at least 5 wt % based on the acidic aqueous solution at from −10° C. to 30° C. to form a hyaluronic acid gel and treating the gel with a neutralizing liquid, (7) a gel made of hyaluronic acid alone which is hardly soluble in a neutral aqueous solution and has transparency, (8) the hyaluronic acid gel according to (7), which dissolves in a neutral aqueous solution at 25° C. in one day to a degree of dissolution of at most 50%, (9) the hyaluronic acid gel according to (7), which dissolves to yield solubilized hyaluronic acid having a branched structure and partly containing a molecular weight fraction with a branching degree of at least 0.5, when treated under accelerating conditions for acid hydrolysis of hyaluronic acid, (10) a biomedical material containing a gel made of hyaluronic acid alone which has transparency and dissolves in a neutral aqueous solution at 25° C. in one day to a degree of dissolution of at most 50%, (11) a biomedical material containing a gel made of hyaluronic acid alone which satisfies the following requirement and has transparency: the hyaluronic acid gel dissolves to yield solubilized hyaluronic acid having a branched structure and partly containing a molecular weight fraction with a branching degree of at least 0.5, when treated under accelerating conditions for acid hydrolysis of hyaluronic acid, (12) a biomedical material containing a hyaluronic acid gel having transparency and un-gelled hyaluronic acid, wherein the hyaluronic acid gel dissolves in a neutral aqueous solution at 25° C. in one day to a degree of dissolution of at most 50%, and dissolves to yield solubilized hyaluronic acid having a branched structure and partly containing a molecular weight fraction with a branching degree of at least 0.5, when treated under accelerating conditions for acid hydrolysis of hyaluronic acid, (13) the biomedical material according to any one of (10) to (12), wherein the hyaluronic acid gel having transparency is flaky, (14) the biomedical material according to any one of (10) to (13), which is an injection for treatment of arthrosis, (15) the biomedical material according to any one of (10) to (13), which is an embolizing material, (16) the biomedical material according to any one of (10) to (13), which is an injection for a soft tissue, and (17) the biomedical material according to any one of (10) to (13), which is an artificial vitreous body.

The present invention provides a hardly water soluble hyaluronic acid gel made of hyaluronic acid alone with transparency. The hyaluronic acid gel according to the present invention retains the structure of the biologically inherent hyaluronic acid by virtue of obviation of use of crosslinkers, and is excellently safe and biocompatible. Therefore, it is useful as a biomedical material such as an injection for treatment of arthrosis, an embolizing material, an injection for a soft tissue and an artificial vitreous body.

BEST MODE FOR CARRYING OUT THE INVENTION

Figure 1:
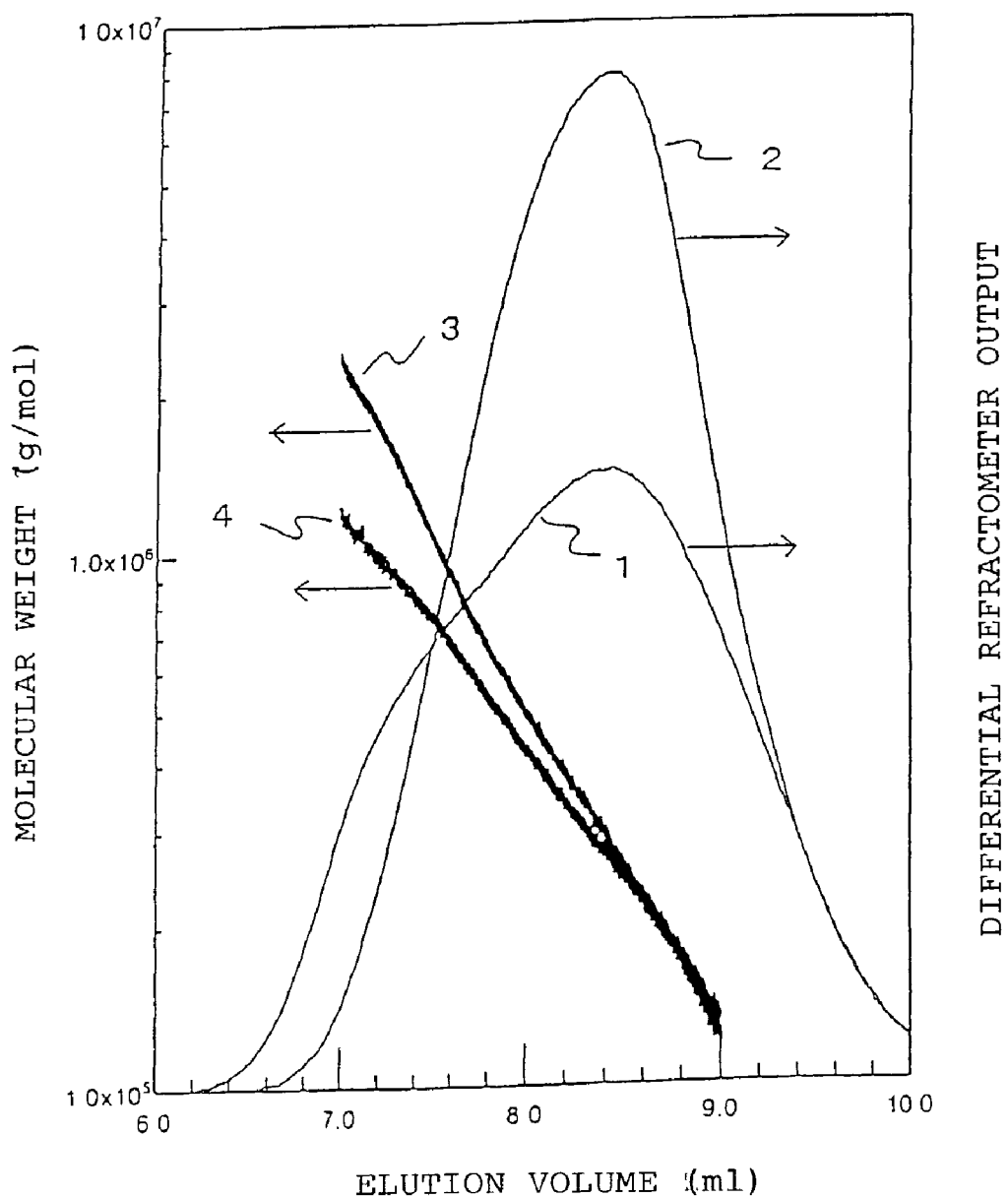
FIG. 1 is a graph that shows the comparison between GPC chromatograms and the molecular weights of the respective fractions obtained in Example 10 and Comparative Example 3.

Now, the present invention will be described below in detail.

In the present invention, hyaluronic acid obtained by extraction from animal tissues or by fermentation may be used without any restriction on its source.

The strain used in fermentation is preferably a hyaluronic acid-producing microorganism isolated from nature such as the genus *Streptococcus* or a mutant which steadily produces hyaluronic acid in high yield such as *Streptococcus equi* FM-100 (accession number 9027 given by National Institute of Bioscience and Human-Technology) disclosed in JP-A-63-123392 or *Streptococcus equi* FM-300 (accession number 2319 given by National Institute of Bioscience and Human-Technology) disclosed in JP-A-2-234689. Pure hyaluronic acid obtained from cultures of the above-mentioned mutants may be used.

The molecular weight of the hyaluronic acid to be used in the present invention is preferably within the range of from about $1 \times 10^5$ to about $1 \times 10^7$ Da. Hyaluronic acid having a higher molecular weight may also be used after the molecular weight is lowered into this range by treatment such as hydrolysis.

In the present invention, the concept of hyaluronic acid is used so as to include its alkali metal salts such as sodium, potassium and lithium salts, too.

In the present invention, by hyaluronic acid alone, it is meant that no chemical crosslinker or chemical modifier is used other than hyaluronic acid, that hyaluronic acid is not in the form of a complex with a cationic polymer, and that the gel is an auto-crosslinked gel.

On the other hand, substances which do not directly induce introduction of a crosslinked structure into hyaluronic acid or make hyaluronic acid insoluble or hardly soluble may be added when the hyaluronic acid gel according to the present invention is prepared.

Further, in preparation of a hyaluronic acid gel, pharmacologically or physiologically active substances may be added to give a hyaluronic acid gel containing such substances without any restriction.

The hyaluronic acid gel according to the present invention is characterized in that it is hardly soluble in a neutral aqueous solution.

In the present invention, the difficulty in dissolution is defined by the solubility in a neutral aqueous solution at 25° C. and means that the gel dissolves in a neutral aqueous solution at 25° C. in 12 hours to a degree of dissolution of at most 50%, preferably at most 30%, particularly preferably at most 10%.

The hyaluronic acid gel according to the present invention is a polymer having a three dimensional network structure or its swollen product. The three dimensional network structure is made of crosslinked hyaluronic acid.

The hyaluronic acid gel according to the present invention can be solubilized through degradation by treatment under accelerating conditions for acid hydrolysis of hyaluronic acid. When the solubilized hyaluronic acid retains the crosslinked structure, it is distinguished as branched hyaluronic acid from linear hyaluronic acid according to the theory of polymer solution.

The accelerating conditions for acid hydrolysis of hyaluronic acid according to the present invention are preferably such that the pH of the aqueous solution is 1.5 and the temperature is 60° C. It is well known that cleavage of the main chain of hyaluronic acid through hydrolysis of glycosidic bonds is remarkably accelerated in an acidic or alkaline aqueous solution as compared with that in a neutral aqueous solution. In addition, acid hydrolysis is accelerated at a higher temperature.

In the present invention, the molecular weights and branching degrees of the fractions separated by GPC according to molecular weight are measured on-line continuously by the GPC-MALLS method. In the present invention, the branching degree was measured by the elution volume method which compares the molecular weight of each fraction of the solubilized hyaluronic acid with the molecular weight of a fraction at the same elution volume of linear hyaluronic acid as a control. The branching degree is the number of branch points in one polymer chain of the solubilized hyaluronic acid and plotted against the molecular weight of the solubilized hyaluronic acid. Measurement of the branching degree by the GPC-MALLS method by the elution volume method is described in PCT/JP98/03536.

Solubilized hyaluronic acid was diluted with the GPC eluent for concentration adjustment and filtered through a membrane filter of 0.2 μm before measurement.

If the hyaluronic acid gel according to the present invention has a crosslinked structure which is stable under accelerating conditions for acid hydrolysis of hyaluronic acid, a branched structure is recognized in the solubilized hyaluronic acid according to the theory of polymer solution. The hyaluronic acid gel according to the present invention has a branching degree of at least 0.5.

In the present invention, transparency means that the visible light transmittance of the hyaluronic acid gel of the present invention in a spectrometric cuvette of 10 mm thick measured at 340 nm to 800 nm is at least 50%, preferably 70%, particularly preferably 90%, based on the transmittance of water.

The transparent hyaluronic acid gel of the present invention is obtained by keeping hyaluronic acid in water at a hyaluronic acid concentration of at least 5 wt % in the presence of an acid component in an amount at least equimolar with the carboxyl groups in the hyaluronic acid, without freezing.

The amount of the acid component to be used for acidification in the present invention is usually preferred to be at least equimolar with the carboxyl groups in hyaluronic acid, although it is set depending on various factors such as the type of the counterion in the hyaluronic acid salt, the molecular weight of hyaluronic acid, the concentration of hyaluronic acid and the properties of the resulting gel such as strength.

As the acid component, any acid that is stronger than hyaluronic acid in acidity may be used. Preferably, a strong acid such as hydrochloric acid, nitric acid and sulfuric acid is used to decrease the amount of an acid.

When the hyaluronic acid concentration is below 5 wt %, a hyaluronic acid gel is not obtained, whether or not a sufficient proportion of the carboxyl groups in the hyaluronic acid undergo protonation.

In the present invention, it is necessary to put hyaluronic acid, water and an acid component in an amount at least equimolar with the carboxyl groups in the hyaluronic acid together so that the hyaluronic acid concentration is 5 wt %, and then keep their coexistence so that gellation proceeds, for example, by letting them stand until a certain period of time passes.

Further, though the keeping temperature and time are set depending on various factors such as the type of the counterion in the hyaluronic acid salt, the molecular weight of hyaluronic acid, the concentration of hyaluronic acid and the properties of the resulting gel such as strength, the temperature is preferably from −10° C. to 30° C. to prevent water from freezing and prevent acid decomposition of hyaluronic acid.

If the acidic hyaluronic acid aqueous solution freezes, an opaque hyaluronic acid gel is obtained.

The acidic hyaluronic acid aqueous solution with a hyaluronic acid concentration of at least 5 wt % to be used in the present invention may be prepared by any methods, for example, by mixing hyaluronic acid with an acidic aqueous solution, by impregnating hyaluronic acid with an acidic aqueous solution, by concentrating a low concentration acidic hyaluronic acid aqueous solution to a predetermined concentration or by adding an acid component to a dense hyaluronic acid aqueous solution.

In the present invention, hyaluronic acid may be used in any form, for example, in powdery form, in the form of a molded block obtained from hyaluronic acid powder by compacting or in the form of a cast film or a sponge obtained from an aqueous solution of hyaluronic acid in distilled water by air-drying or freeze-drying. The mixing of hyaluronic acid with an acidic aqueous solution may be accomplished by addition of the acidic aqueous solution to hyaluronic acid and subsequent kneading.

The impregnation of hyaluronic acid with an acidic aqueous solution may be conducted so as to attain a predetermined hyaluronic acid concentration.

In the case where a dilute acidic hyaluronic acid aqueous solution is concentrated to a predetermined concentration, the low concentration acidic hyaluronic acid aqueous solution is prepared firstly by adding an acid component to hyaluronic acid dissolved in distilled water or dissolving hyaluronic acid directly in an acidic aqueous solution and may be prepared from any form of hyaluronic acid. The low concentration is intended to be lower than the hyaluronic acid concentration of the intended hyaluronic acid gel and is preferably lower than 5 wt % for easy handling. The concentration may be accomplished by ultracentrifugation, air-drying, vacuum drying or freeze-drying.

In the case where an acid component is added to a dense hyaluronic acid aqueous solution, the dense hyaluronic acid aqueous solution is prepared firstly by mixing hyaluronic acid with distilled water or by concentrating a dilute hyaluronic acid aqueous solution and may be prepared from any form of hyaluronic acid. The addition of an acid component to the dense hyaluronic acid aqueous solution may be accomplished by exposure to an atmosphere of a gaseous acid such as hydrogen chloride or by immersion in a solution of an acid in a solvent with little solvency for hyaluronic acid such as an ethanol-hydrochloric acid solution.

The hyaluronic acid gel obtained in accordance with the present invention has to be subjected to neutralization of hyaluronic acid in the acid form in which the carboxyl groups have protonated and the acid component used for acidification in order to avoid acid hydrolysis of hyaluronic acid. For neutralization, an aqueous solvent such as phosphate buffer or aqueous sodium hydroxide is usually used, though there is no restriction on the aqueous solvent so long as it does not functionally impair the hyaluronic acid gel.

Herein, such a solvent is generically referred to as a neutralizing liquid.

Although there is no particular restriction on the treatment with a neutralizing liquid (the neutralization method), a batch method, a filtration method or a method in which a solvent is passed through a loaded column is usually used. The neutralization conditions, inclusive of the volume of the neutralization liquid and the number of times of neutralization, may be selected appropriately considering the shape and the use of the hyaluronic acid gel so that hyaluronic acid in the acid form and the acid component used for acidification are neutralized.

The hyaluronic acid gel treated with a neutralizing liquid is used in an immersed state with a solvent, in a wet state with a solvent or in a dry state after air-drying, vacuum drying or freeze drying depending on the use.

With a view to shaping the hyaluronic acid gel, by selecting hyaluronic acid, the vessel for the acidic hyaluronic acid aqueous solution and the procedure, a hyaluronic acid gel of desired shape such as a sheet-like, filmy, flaky, spongy, massive or tubular shape can be obtained. For example, from compacted hyaluronic acid power, a gel in the form of a block or a sheet is obtained. Preparation of a hyaluronic acid gel may be followed by post-treatment such as mechanical fragmentation, freezing-thawing, rolling or spinning to make the gel into fine flakes, a sponge, a film or the like.

The hyaluronic acid gel of the present invention is obtainable endotoxin-free and aseptically if care is taken over the reagents, water and the vessels.

The hyaluronic acid gel thus prepared is transparent in itself and retains transparency even after crushed and suspended. It may be filled into a syringe or a bag before use. If pharmaceutically or physiologically active substances are added at the time of gelation, the resulting hyaluronic acid gel contains these substances in it.

For example, addition of thrombin which coagulates blood by catalyzing conversion of fibrinogen into fibrin in the blood coagulation cascade with a view to accelerating embolization and addition of various antitumor agents with a view to obstructing tumor arteries may be mentioned without any restriction.

The hyaluronic acid gel of the present invention shows great improvement in in vivo residency and persistency over hyaluronic acid solution and excellently safe and biocompatible by virtue of the absence of crosslinkers. Therefore, it can be used as a biomedical material such as an injection for treatment of arthrosis, an embolizing material, an injection for a soft tissue and an artificial vitreous body.

EXAMPLES

Now, the present invention will be described in further detail with reference to Examples. However, the present invention is by no means restricted to these specific Examples.

EXAMPLE 1

100 mg of powdery sodium hyaluronate (molecular weight calculated from limiting viscosity: $2 \times 10^6$ Da) was compacted at 3000 N/cm$^2$ for 3 minutes into a rectangular molding of 8 mm×8 mm×2 mm. The molding was impregnated with 570 mg of 1 mol/l hydrochloric acid in a rectangular styrene vessel so that the hyaluronic acid concentration would be 15 wt %, sealed in the vessel and kept still in a refrigerator set at 5° C. for 6 days to give a rectangular transparent hyaluronic acid gel.

EXAMPLE 2

The same procedure as in Example 1 was followed except that 1 mol/l hydrochloric acid was used in an amount of 1330 mg for impregnation so that the hyaluronic acid concentration would be 7 wt % to give a rectangular transparent hyaluronic acid gel.

EXAMPLE 3

The same procedure as in Example 1 was followed except that hyaluronic acid (molecular weight calculated from limiting viscosity: $9 \times 10^6$ Da) was used instead, and the molding was kept still in a refrigerator set at 5° C. for 17 days to give a rectangular transparent hyaluronic acid gel.

EXAMPLE 4

The same procedure as in Example 1 was followed except that 0.45 mol/l hydrochloric acid was used, and the molding was kept still in a refrigerator set at 5° C. for 17 days to give a rectangular transparent hyaluronic acid gel.

EXAMPLE 5

The same procedure as in Example 1 was followed except that the molding was kept still at 25° C. for 3 days to give a rectangular transparent hyaluronic acid gel.

EXAMPLE 6

Sodium hyaluronate (molecular weight calculated from limiting viscosity: $2 \times 10^6$ Da) was dissolved in distilled water to give 1 wt % hyaluronic acid aqueous solution. The hyaluronic acid aqueous solution was air-dried on a glass plate at 80° C. to give a cast film of about 200 µm thick. The same procedure as in Example 1 was followed with the cast film to give a transparent hyaluronic acid gel sheet.

EXAMPLE 7

100 mg of powdery sodium hyaluronate (molecular weight calculated from limiting viscosity: $2 \times 10^6$ Da) was put in a 50 ml glass bottle, and 900 mg of 1 mol/l hydrochloric acid was added so that the hyaluronic acid concentration would be 10 wt %. They were mixed by means of a spatula, sealed in the bottle and kept still in a refrigerator set at 5° C. for 8 days to give a transparent hyaluronic acid gel.

EXAMPLE 8

Powdery sodium hyaluronate (molecular weight calculated from limiting viscosity: $2 \times 10$ Da) was dissolved in 1 mol/l hydrochloric acid to give 1 wt % hyaluronic acid aqueous solution. The hyaluronic acid solution was subjected to ultracentrifugation and found to be concentrated to a hyaluronic acid concentration of 18 wt % after removal of the supernatant. The concentrated hyaluronic acid solution was kept still in a refrigerator set at 5° C. for 3 days to give a transparent hyaluronic acid gel.

The ultracentrifugation was done by using an ultracentrifugator CS120EX, Hitach Koki Co., Ltd., a rotor S100AT5 and sample tubes 4PC at 99000 rpm at 5° C. for 24 hours.

COMPARATIVE EXAMPLE 1

The same procedure as in Example 1 was followed except that distilled water was used instead of 1 mol/l hydrochloric acid. As a result, not a transparent hyaluronic acid gel, but a thick transparent hyaluronic acid solution was obtained.

COMPARATIVE EXAMPLE 2

The same procedure as in Example 1 was followed except that 3230 mg of 1 mol/l hydrochloric acid was used for impregnation so that the hyaluronic acid concentration would be 3 wt %. As a result, not a transparent hyaluronic acid gel, but a thick transparent hyaluronic acid solution was obtained.

EXAMPLE 9

Solubility Test for Hyaluronic Acid Gels

A phosphate buffer was added to physiological saline at a concentration of 50 mM to give a phosphate buffer-physiological saline at pH 7.0. The hyaluronic acid gels obtained were immersed in 50 ml of the phosphate buffer-physiological saline based on 10 mg of dry hyaluronic acid in the gels. Similarly, the thick hyaluronic acid solution obtained in Comparative Example 1 was immersed in 50 ml of the phosphate buffer-physiological saline based on 10 mg of dry weight. The degree of dissolution of hyaluronic acid in the phosphate buffer-physiological saline at 25° C. under stirring was obtained from the concentration of hyaluronic acid in the phosphate buffer-physiological saline.

Namely, the solubility of a hyaluronic acid gel in a neutral aqueous solution at 25° C. is defined according to this test.

Measurement of Hyaluronic Acid Concentration

The concentration of hyaluronic acid in the phosphate buffer-physiological saline was obtained from the area of a GPC peak by using a differential refractometer as a detector.

As described above, the solubility test was actually carried out on the hyaluronic acid gels obtained in Examples 1 to 8 and in Comparative Examples 1 and 2. The results were tabulated in Table 1.

TABLE 1

Comparison of solubility

| Test No. | Sample | Degree of dissolution (%) | | | Remarks |
| --- | --- | --- | --- | --- | --- |
| | | After 1 day | After 7 days | After 14 days | |
| 1 | Transparent HA gel obtained in Example 1 | 0 | 1 | 11 | Example |
| 2 | Transparent HA gel obtained in Example 2 | 4 | 10 | 19 | Example |
| 3 | Transparent HA gel obtained in Example 3 | 2 | 10 | 25 | Example |
| 4 | Transparent HA gel obtained in Example 4 | 4 | 10 | 28 | Example |
| 5 | Transparent HA gel obtained in Example 5 | 18 | 44 | 94 | Example |
| 6 | Transparent HA gel obtained in Example 6 | 8 | 54 | 100 | Example |
| 7 | Transparent HA gel obtained in Example 7 | 22 | 67 | 100 | Example |
| 8 | Transparent HA gel obtained in Example 8 | 4 | 24 | 56 | Example |
| 9 | Thick solution obtained in Comparative Example 1 | 100 | — | — | Comparative Example |
| 10 | Thick solution obtained in Comparative Example 2 | 100 | — | — | Comparative Example |

HA: hyaluronic acid

For example, in Test No. 1, the degree of dissolution of the hyaluronic acid gel obtained in Example 1 was found to be less than 5% after 1 day, 1% after 7 days and 11% after 14 days. Namely, more than 90% of the hyaluronic acid remained even after 7 days. In contrast, in Tests No. 9 and 10, the degrees of dissolution of the thick hyaluronic acid solutions obtained in Comparative Examples 1 and 2 were found to be 100% after 1 day, which indicates complete dissolution.

Thus, it was found that the thick hyaluronic acid solutions obtained in Comparative Examples 1 and 2 dissolved in water quite quickly (Tests Nos. 9 to 10), whereas the hyaluronic acid gels obtained according to the present invention dissolved very slowly (for example, Tests Nos. 1 to 8).

These results suggest that the hyaluronic acid gel obtained according to the present invention has a long in vivo residence time.

EXAMPLE 10

Solubilization Test for Hyaluronic Acid Gels

The pH of distilled water was adjusted to 1.5 with hydrochloric acid. The hyaluronic acid gel obtained in Example 1 was immersed in the phosphate buffer-physiological saline mentioned in Example 9 and then withdrawn from the phosphate buffer-physiological saline. The hyaluronic acid gel was immersed in 15 ml of aqueous hydrochloric acid at pH 1.5, based on 15 mg of dry hyaluronic acid and hydrolyzed in an oven set at 60° C. 0.5 ml samples were withdrawn after 1 hour, after 2.5 hours and after 5 hours. After 2.5 hours, the hyaluronic acid gel had disappeared almost completely and was not visually recognizable.

COMPARATIVE EXAMPLE 3

Sodium hyaluronate (molecular weight calculated from limiting viscosity: $2 \times 10^6$ Da) was dissolved in distilled water to give a 0.1 wt % hyaluronic acid aqueous solution. The pH of the aqueous solution was adjusted to 1.5 with 1 mol/l hydrochloric acid. A 15 ml portion of the acidic hyaluronic acid aqueous solution was left in an oven at 60° C. for 4 hours for acid hydrolysis of the linear hyaluronic acid.

EXAMPLE 11

Measurement of Molecular Weight and Branching Degree of Solubilized Hyaluronic Acid For GPC-MALLS measurement, the solubilized hyaluronic acid obtained in Example 10 and the acid hydrolysate of linear hyaluronic acid obtained in Comparative Example 2 were diluted by a factor of 2.5 with the GPC eluent to 0.04 wt % and filtered through a membrane filter of 0.2 $\mu$m, and 0.1 ml portions of them were injected.

The measurement was carried out by using a GPC column SB806HQ (Showa Denko K.K.), a differential refractometer 830-RI (JASCO Corporation) as a detector, a MALLS DAWNDSP-F (Wyatt), 0.2 mol/l aqueous sodium nitrate as the eluent at a temperature of 40° C. at a flow rate of 0.3 ml/min at intervals of 1 datum/2 sec. For the measurement of the intensity of scattering, eight detectors with scattering angles from 21.7° to 90° were used. For data processing, software ASTRA Version 4.10 (Wyatt) was used.

As described above, the solubilized hyaluronic acid obtained in Example 10 and the acid hydrolysate of linear hyaluronic acid obtained in Comparative Example 3 were examined. The results are shown in Table 2.

TABLE 2

| Test No. | Reaction Time (hour) | Weight-average molecular weight Mw | Molecular weight distribution Mw/Mn | Degree of solubilization (%) | Remarks |
|---|---|---|---|---|---|
| 11 | 1 | $36.8 \times 10^4$ | 1.8 | 28 | Example 10 |
| 12 | 2.5 | $58.4 \times 10^4$ | 2.7 | 84 | Example 10 |
| 13 | 6 | $10.7 \times 10^4$ | 1.8 | 97 | Example 10 |
| 14 | 4 | $35.0 \times 10^4$ | 1.7 | — | Comparative Example 3 |

For example, in Test No. 11, it was found that the hyaluronic acid gel obtained in Example 10 was solubilized to a low degree when withdrawn after 1 hour of reaction. In Test No. 13, the sample withdrawn after 6 hours of reaction showed such a low molecular weight that the branching degree was difficult to measure. In Test No. 12, the hyaluronic acid gel was solubilized to a high degree when withdrawn after 2.5 hours of reaction, and the large molecular weight distribution of 2.7 reflects the presence of branched hyaluronic acid.

Figure 2:
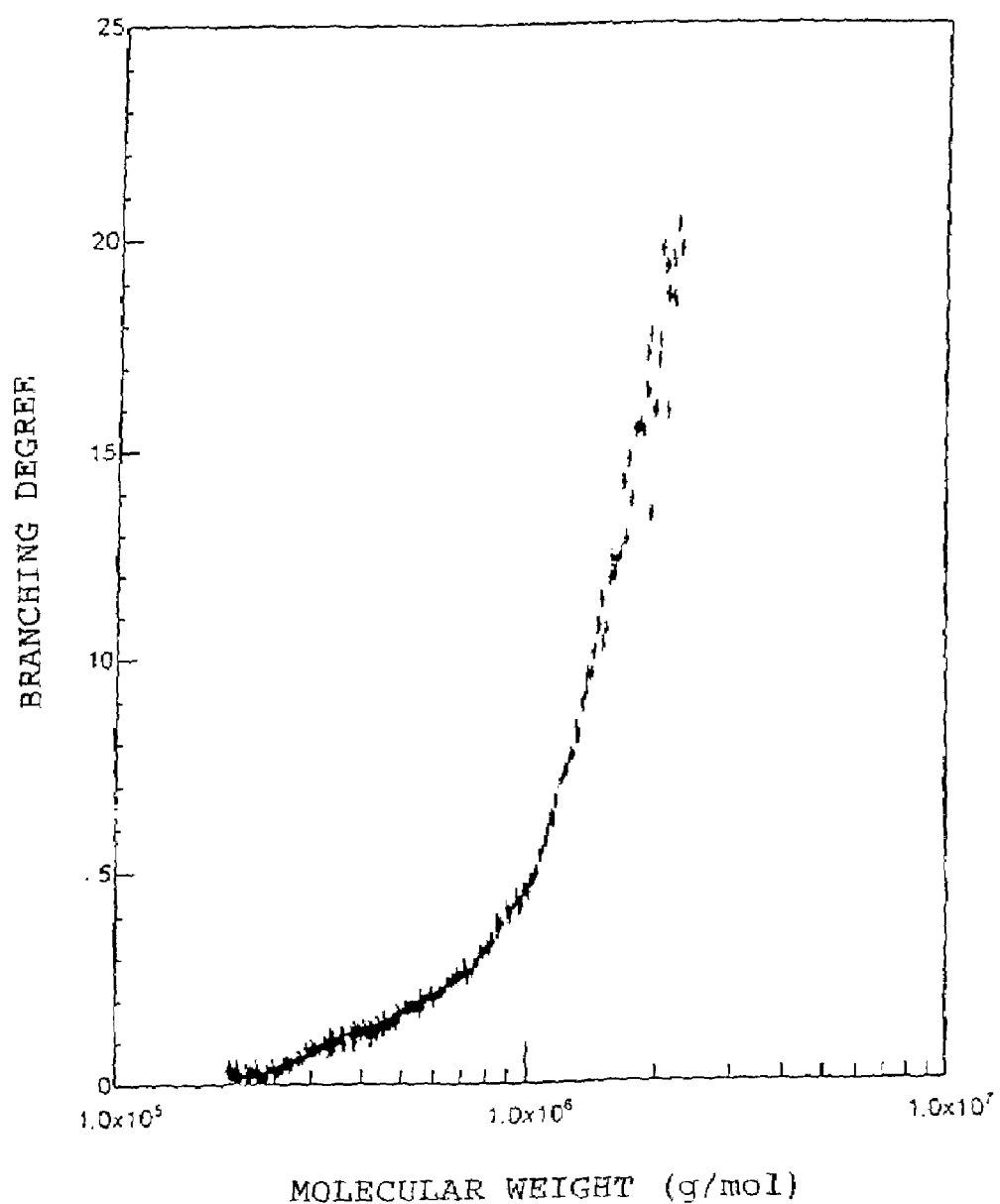
FIG. 2 is a graph that shows the relation between the branching degree and the molecular weight in Example 10 on the basis that the hyaluronic acid in Comparative Example 3 was linear.

The GPC chromatograms of the solubilized hyaluronic acid obtained in Example 10 after 2.5 hours of reaction and the acid hydrolysate of linear hyaluronic acid obtained in Comparative Example 3, and the results of calculation of their branching degrees obtained in Test No. 12 and Test No. 14, respectively, were shown in FIG. 1 and FIG. 2.

FIG. 1 is a graph that shows the comparison between GPC chromatograms and the molecular weights of the respective fractions obtained in Example 10 and Comparative Example 3. Reference numeral 1 denotes the GPC chromatogram obtained in Example 10, reference numeral 2 denotes the GPC chromatogram obtained in Comparative Example 3, reference numeral 3 denotes the molecular weights of the respective fractions obtained in Example 10, and reference numeral 4 denotes the molecular weights of the respective fractions obtained in Comparative Example 3. As is evident from FIG. 1, the GPC chromatogram 1 for Example 10 had a shoulder at a higher molecular weight range than the GPC chromatogram 2 for Comparative Example 3. From comparison of the molecular weights of fractions at the same elution volumes, it was found that the molecular weight for Example 10 was clearly higher than that for Comparative Example 3 within the elution volume range of at most 8.6 ml, which corresponds to the molecular weight range of about 200,000 or larger.

The fractions for Example 10 showed higher molecular weights than the fractions for Comparative Example 3 at the same elution volumes, because of the presence of branched hyaluronic acid.

FIG. 2 shows the relation of the branching degree and the molecular weight for Example 10 calculated on the basis of the linear hyaluronic acid of Comparative Example 3. The branching degree was calculated from the molecular weights of fractions for Example 10 and Comparative Example 3 at the same elution volumes by using equations.

FIG. 2 shows a sharp rise in the branching degree from 0.5 within the molecular weight range of 200,000 or larger for Example 10, which indicates that the hyaluronic acid gel obtained according to the present invention contains a crosslinked structure stable under accelerating conditions for acid hydrolysis of hyaluronic acid. Likewise, the branching degrees of the hyaluronic acid gels obtained in Examples 2 to 8 were at least 0.5.

EXAMPLE 12

Transparent Gel Slurry 0.8 g of the transparent hyaluronic acid obtained in Example 1 gel was put in 80 ml of physiological saline and crushed with a microhomogenizer (Nissei Excel Auto Homogenaizer) to give a crushed hyaluronic acid gel slurry with an average grain size of about 300 $\mu$m. The hyaluronic acid gel was filled into a 2.5 ml syringe (with pistons having a diameter of about 12 mm) manufactured by Terumo Corporation equipped with an injection needle of 21G manufactured by Terumo Corporation, and the force required to eject it at a rate of 0.1 ml/sec was measured (by means of Tensilon EZ Test-20N manufactured by Shimadzu Corporation). The slurry was readily ejected with an ejection force of about 10 N.

EXAMPLE 13

Transparent Gel Composition 0.8 g of the transparent hyaluronic acid gel obtained in Example 1 was put in 40 ml of physiological saline and crushed with a microhomogenizer (Nissei Excel Auto Homognaizer) to give a crushed hyaluronic acid gel slurry with an average grain size of about 300 μm. The slurry was mixed with 40 ml of a hyaluronic acid solution in physiological saline with a hyaluronic acid concentration of 1 wt % to give a hyaluronic acid gel composition.

The ejection force for the hyaluronic acid gel composition was measured by the method described in Example 10, and it was readily ejected with an ejection force of about 12 N.

COMPARATIVE EXAMPLE 4

Hyaluronic Acid Gel Slurry

A hyaluronic acid gel was prepared in the method disclosed in PCT/JP98/03536 and made into a hyaluronic acid gel slurry.

Sodium hyaluronate (molecular weight calculated from limiting viscosity: $2 \times 10^6$ Da) was dissolved in distilled water to give a 1 wt % hyaluronic acid aqueous solution. The aqueous solution was adjusted to pH 1.5 with 1N nitric acid to give an acidic hyaluronic acid aqueous solution.

A 50 ml portion of the acidic hyaluronic acid aqueous solution was put in a 50 ml metal vessel and placed in a refrigerator set at −20° C. After 120 hours, it was taken out and thawed at 25° C. to give a hyaluronic acid gel. The gel was dialyzed against distilled water sufficiently for removal of the excessive acid and sodium chloride, then dialyzed against 25 mmol/l phosphate buffer-physiological saline at pH 7 for neutralization, sufficiently dialyzed against distilled water again and freeze-dried to give a hyaluronic acid gel sheet. 100 mg of the hyaluronic acid gel was put in 10 ml of 25 mmol/l phosphate buffer-physiological saline and crushed with a microhomogenizer (Polytoron, Kinematica AG) to give a hyaluronic acid gel slurry.

EXAMPLE 14

Transparency Test

The hyaluronic acid gels obtained in Examples 1 to 8, 12 and 13 and the hyaluronic acid gel slurry obtained in Comparative Example 4 were filled into spectrometric cuvettes of 10 mm thick, and the transmittances against visible light of from 340 nm to 800 nm based on the transmittance of water were measured (by means of Beckman spectrophotometer DU-64). The results are shown in Table 3. The transmittance in Table 3 were measured within the above-mentioned range. As the control, a 1 wt % hyaluronic acid aqueous solution in phosphate buffer-physiological saline was used.

TABLE 3

Comparison of transparency

| Test No. | Sample | Transmittance (%) (min–max) | Remarks |
|---|---|---|---|
| 15 | Transparent HA gel of Example 1 | 92–95 | Example |
| 16 | Transparent HA gel of Example 2 | 95–98 | Example |
| 17 | Transparent HA gel of Example 3 | 93–95 | Example |
| 18 | Transparent HA gel of Example 4 | 90–96 | Example |
| 19 | Transparent HA gel of Example 5 | 92–98 | Example |
| 20 | Transparent HA gel of Example 6 | 91–95 | Example |
| 21 | Transparent HA gel of Example 7 | 92–95 | Example |
| 22 | Transparent HA gel of Example 8 | 92–97 | Example |
| 23 | Transparent HA gel slurry of Example 12 | 93–98 | Example |
| 24 | Transparent HA gel composition of Example 13 | 95–100 | Example |
| 25 | HA gel slurry of Comparative Example 4 | 6–8 | Comparative Example |
| 26 | 1 wt % HA solution | 99–100 | Control |

From Table 3, it is evident that the samples obtained in Examples 1 to 8, 12 and 13 were transparent.

EXAMPLE 15

Comparison of Retention in Rabbit Articular Cavity

Both knees of male adult normal New Zealand White rabbits weighing 2.5 to 3.0 kg were shorn with an electric clipper and disinfected. 1% aqueous solution of the transparent gel slurry obtained in Example 12, the transparent gel composition obtained in Example 13 or hyaluronic acid (molecular weight calculated from limiting viscosity: $2 \times 10^6$ Da) in physiological saline was administered into the left knee articular cavities at a dose of 0.1 ml/kg weight, and physiological saline was administered into the right knee articular cavities at a dose of 0.1 ml/kg weight as a control. After the administration, synovial fluid was taken from both knees every two days, and the hyaluronic acid concentrations of the synovial fluid samples were determined by GPC.

The persistence was calculated from the following equation wherein the intrinsic hyaluronic acid is the hyaluronic acid content of the synovial fluid sample taken from a articular cavity immediately after administration of physiological saline.

Persistence (%)=(Recovery−Intrinsic hyaluronic acid content)/dosage×100

The results are shown in Table 4.

TABLE 4

Comparison of retention hyaluronic acid persistence (%) mean:
n = 3

| Test No. | Sample | 2 days | 4 days | 6 days | 8 days | 10 days | 12 days | 14 days | Remarks |
|---|---|---|---|---|---|---|---|---|---|
| 27 | Transparent HA gel slurry of Example 12 | 91 | 70 | 33 | 15 | 7 | 2 | 0 | Example |
| 28 | Transparent HA gel composition of Example 13 | 92 | 79 | 40 | 21 | 12 | 4 | 0 | Example |
| 29 | 1% HA solution | 45 | 6 | 0 | NT | NT | NT | NT | Comparative Example |

(Note) NT denotes not tested.

From Table 4, it is evident that the crushed hardly water-soluble hyaluronic acid gel has much better in vivo persistence than the hyaluronic acid solution.

EXAMPLE 16

Bradykinin-Induced Pain Suppression Effect

Into the hind limb knee articular cavities of female beagles weighing about 10 kg, the transparent gel slurry obtained in Example 12 (0.3 ml/kg body mass), the transparent gel composition obtained in Example 13 (0.3 ml/kg body mass), a 1% hyaluronic acid aqueous solution (molecular weight calculated from limiting viscosity: $2 \times 10^6$ Da, 1% solution in physiological saline, 0.3 ml/kg body mass) or physiological saline as a control (0.3 ml/kg body mass) was administered first, and 2, 4 and 7 days after administration, an aqueous solution of bradykinin, a pain-producing substance, in physiological saline (BK: 0.2 µg/ml, 0.05 ml/kg body mass) was administered. The pain suppression effect was determined on the basis of the body mass proportion loaded on a painful limb between 1 and 2 minutes, 3 and 4 minutes and 5 and 6 minutes after. The results are shown in Table 5. The body mass proportion is represented by the following equation.

TABLE 5

Comparison of joint pain suppression effect

Body mass proportion
(%) mean: n = 10

| Test No. | Sample | After 2 days | After 4 days | After 7 days | Remarks |
|---|---|---|---|---|---|
| 30 | Transparent HA gel slurry of Example 12 | 70 | 68 | 46 | Example |
| 31 | Transparent HA gel composition of Example 13 | 73 | 71 | 55 | Example |
| 32 | 1% HA solution | 60 | 39 | 26 | Comparative Example |

TABLE 5-continued

Comparison of joint pain suppression effect

Body mass proportion
(%) mean: n = 10

| Test No. | Sample | After 2 days | After 4 days | After 7 days | Remarks |
|---|---|---|---|---|---|
| 33 | Control (physiological saline) | 27 | 25 | 29 | Comparative Example |

$$\text{Body mass proportion (\%)} = \frac{\text{(Mean body mass proportion loaded on a subject limb at a predetermined time after BK administration)}}{\text{(Mean body mass proportion loaded on a subject limb for a 1 minute period before BK administration)}} \times 100$$

From Table 5, it is evident that the transparent gel slurry and transparent gel composition maintained their pain suppression effect even after 7 days while the suppression effects of the hyaluronic acid solution diminished to the same level as the control in 7 days.

EXAMPLE 17

Preparation of Thrombin-Containing Transparent Gel Slurry

To the transparent gel slurry obtained in Example 17, thrombin in solution was added in an amount of 0.5 NIH unit per 100 mg to obtain a thrombin-containing fluid hyaluronic acid gel.

EXAMPLE 18

Embolization Test

The thrombin-containing transparent gel slurry obtained in Example 17 was sucked into an injector and intra-arterially administered into the auricles of New Zealand White rabbits weighing about 2.5 kg at a dose of about 0.1 ml. The injected gel quickly coagulated, developing visible recognizable obstruction.

No change was seen during 1 month morphological observation, and a histological postmortem examination of the emboli revealed satisfactory obstruction.

1.0 wt % hyaluronic acid solution as a control did not embolize.

EXAMPLE 19

Administration Test on Guinea Pigs

The transparent gel slurry obtained in Example 12, the transparent gel composition obtained in Example 13 and 0.5 wt % aqueous solution of sodium hyaluronate (molecular weight calculated from limiting viscosity: $2 \times 10^6$) in physiological saline were hypodermically administered into twenty female Hartray guinea pigs weighing 350 to 400 g under anaesthesia at a dose of 0.05 ml, 10 sites per individual. 0, 1, 2, 3 and 4 weeks after, the tissues of the respective sites were sampled from one of each administration group. They were sectioned after fixation and embedding, and the sections were stained with hematoxylin-eosin and Alcian Blue and histologically examined under a microscope.

The results indicate that the when the samples obtained in Examples 12 and 13 were administered, the skin maintained in the same state as immediately after the administration and contained hyaluronic acid in the tissue even after 4 weeks, while 1.0 wt % hyaluronic acid aqueous solution in physiological saline was absorbed completely in 4 weeks. No exudation from cells was observed that suggests inflammatory reactions.

EXAMPLE 20

Refractive Index Measurement

The refractive indices of the transparent gel slurry obtained in Example 12 and the transparent gel composition obtained in Example 13 at 20° C. were measured by means of an Abbe refractometer (manufactured by Atago) and found to be similar to that of the vitreous body, 1.335 and 1.334, respectively.

EXAMPLE 21

Effect on Rabbit Retinal Detachment

Fifteen white rabbits (New Zealand White) weighing from 2.5 to 3.0 kg were (15 eyes) were subjected to retrobulbar anaesthetization with 2% lidocaine hydrochloride following induction of mydriasis by instillation of 0.5% indomethacin and 5% phenylephrine hydrochloride.

After eye washing and periocular disinfection, a rabbit was anchored under a surgical microscope, and the conjunctiva and the cornea were incised. The sclera was incised, and a perfusion tap was inserted. The sclera was incised further for insertion of a vitreous adenotome and a light guide, and a vitreous adenotome and a light guide were inserted.

After vitrectomy with the vitreous adenotome under suction, a needle of 21G with a curved tip was inserted instead of the vitreous adenotome. The needle of 21G was inserted on the epiotic side of the retina, and about 0.1 mp of sterilized air was introduced to below the retina to partly detach the retina. After the detachment, a vitreous adenotome was inserted again to form a slit by partial incision on the peeled retina.

After replacement of the persulate with air, the transparent gel slurry obtained in Example 12 or the transparent gel composition obtained in Example 13 was injected into the vitreous cavity to bring back the retina through replacement of the air. The probe of a laser beam intraocular photocoagulator was inserted into the vitreous cavity for intraocular coagulation, and the scleral incision and the conjunctival incision were closed with a 8-0 nylon suture.

The results of microscopic analysis after about a month revealed that the samples obtained in Examples 12 and 13 induced no abnormal symptoms such as reccurent retinal detachment and the photocoagulated site cicatrized satisfactorily. Neither vitreous clouding nor inflammatory reactions were not observed under a slit lump.

What is claimed is:

1. A biomedical material which contains a transparent gel consisting of hyaluronic acid or a salt thereof; a second acid or a salt thereof; and water;
    wherein the transparent gel does not contain any cross-linkers, and
    wherein at least one of the following requirements (a), (b) and (c) is satisfied:
    (a) the hyaluronic acid gel dissolves in a neutral aqueous solution at 25° C. in one day to a degree of dissolution of at most 50%,
    (b) the hyaluronic acid gel dissolves to yield a solubilized hyaluronic acid having a branched structure and partly containing a molecular weight fraction with a branching degree of at least 0.5, when treated under accelerating conditions for acid hydrolysis of hyaluronic acid, or
    (c) the hyaluronic acid gel satisfies the above requirements (a) and (b), and the biomedical material also contains an un-gelled hyaluronic acid.

2. The biomedical material according to claim 1, wherein the hyaluronic acid gel is flaky.

3. A biomedical material according to claim 1, which is an injection for treatment of arthrosis.

4. The biomedical material according to claim 1, which is an embolizing material.

5. The biomedical material according to claim 1, which is an injection for soft tissue.

6. The biomedical material according to claim 1, which is an artificial vitreous body.

7. The biomedical material according to claim 1, wherein the hyaluronic acid is an alkali metal salt of hyaluronic acid.

8. The biomedical material according to claim 1, wherein the hyaluronic acid is auto-cross-linked.

9. The biomedical material according to claim 1, wherein the hyaluronic acid gel dissolves in a neutral aqueous solution at 25° C. in one day to a degree of dissolution of at most 30%.

10. The biomedical material of claim 1, wherein the hyaluronic acid gel dissolves in a neutral aqueous solution at 25° C. in one day to a degree of dissolution of at most 10%.

11. The biomedical material of claim 1, wherein each of requirements (a), (b) and (c) is satisfied.

12. The biomedical material of claim 1, wherein requirement (a) is satisfied.

13. The biomedical material of claim 1, wherein requirement (b) is satisfied.

14. The biomedical material of claim 1, wherein the hyaluronic acid gel has a transparency of at least 90%.

15. The biomedical material of claim 1, wherein the hyaluronic acid gel has a transparency of at least 95%.

16. The biomedical material of claim 1, wherein the hyaluronic acid is present in the hyaluronic acid gel in an amount of at least 5% by weight.

17. The biomedical material of claim 1, wherein the hyaluronic acid is present in the hyaluronic acid gel in an amount of from 7 to 18% by weight.

18. The biomedical material of claim 1, wherein the second acid is hydrochloric acid.

19. The biomedical material of claim 1, wherein the second acid is present in at least an equimolar amount with the carboxylic groups of the hyaluronic acid.

20. The biomedical material of claim 1, wherein the hyaluronic acid gel is obtained by mixing a hyaluronic acid solid with an aqueous solution of the second acid to form a mixture and refrigerating the mixture.

21. The biomedical material of claim 1, wherein the hyaluronic acid is not in the form of a complex with a cationic polymer.

* * * * *